(12) United States Patent
McWeeney

(10) Patent No.: US 7,485,150 B2
(45) Date of Patent: Feb. 3, 2009

(54) DRAINAGE DEVICES AND METHODS

(75) Inventor: John O. McWeeney, Brighton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 674 days.

(21) Appl. No.: 10/128,070

(22) Filed: Apr. 23, 2002

(65) Prior Publication Data

US 2003/0199805 A1    Oct. 23, 2003

(51) Int. Cl.
*A61F 2/04* (2006.01)
(52) U.S. Cl. .................................. 623/23.64
(58) Field of Classification Search .......... 604/8–10, 604/284, 94.01, 19, 540–544, 435, 249, 585, 604/524; 623/23.64–23.66, 23.7, 23.69
See application file for complete search history.

(56) References Cited

U.S. PATENT DOCUMENTS

| | | | | |
|---|---|---|---|---|
| 4,134,402 | A | 1/1979 | Mahurkar | 128/214 |
| 4,202,332 | A | 5/1980 | Tersteegen et al. | 128/214.4 |
| 4,403,983 | A | 9/1983 | Edelman et al. | 604/43 |
| 4,531,933 | A * | 7/1985 | Norton et al. | 604/8 |
| 4,574,000 | A * | 3/1986 | Hunter | 623/23.64 |
| 4,583,968 | A | 4/1986 | Mahurkar | 604/43 |
| 4,782,834 | A | 11/1988 | Maguire et al. | 128/344 |
| 5,019,102 | A * | 5/1991 | Hoene | 623/23.66 |
| 5,057,073 | A | 10/1991 | Martin | 604/43 |
| 5,100,395 | A * | 3/1992 | Rosenberg | 604/284 |
| 5,176,626 | A | 1/1993 | Soehendra | |
| 5,514,088 | A * | 5/1996 | Zakko | 604/31 |
| 5,681,274 | A * | 10/1997 | Perkins et al. | 604/8 |
| 5,695,457 | A * | 12/1997 | St. Goar et al. | 604/4.01 |
| 5,891,111 | A * | 4/1999 | Ismael | 604/541 |
| 5,913,852 | A * | 6/1999 | Magram | 604/540 |
| 5,957,912 | A * | 9/1999 | Heitzmann | 604/533 |
| 6,086,553 | A * | 7/2000 | Akbik | 604/8 |
| 6,102,888 | A * | 8/2000 | Walker | 604/28 |
| 6,206,849 | B1 | 3/2001 | Martin et al. | 604/43 |
| 6,332,892 | B1 * | 12/2001 | Desmond et al. | 623/1.15 |
| 6,364,868 | B1 * | 4/2002 | Ikeguchi | 604/514 |
| 6,524,268 | B2 * | 2/2003 | Hayner et al. | 604/8 |
| 6,569,150 | B2 * | 5/2003 | Teague et al. | 604/524 |
| 6,626,858 | B2 * | 9/2003 | Lynch et al. | 604/8 |
| 6,648,863 | B2 * | 11/2003 | Reever | 604/327 |
| 6,656,146 | B1 * | 12/2003 | Clayman et al. | 604/8 |
| 2001/0053936 | A1 | 12/2001 | Whitmore | |
| 2002/0033180 | A1 * | 3/2002 | Solem | 128/898 |

FOREIGN PATENT DOCUMENTS

| | | |
|---|---|---|
| DE | 42 13 480 A | 10/1993 |
| WO | WO 96-11721 A | 4/1996 |
| WO | WO 97 17094 A | 5/1997 |

* cited by examiner

*Primary Examiner*—Corrine McDermott
*Assistant Examiner*—Christopher D Prone

(57) ABSTRACT

A ureteral drainage stent is designed to be placed in a patient's ureter and extend into a patient's bladder. An ureteral drainage stent includes a distal region for placement in the ureter and renal cavity, and a proximal region for placement in a urinary bladder and urethra. The distal region includes an elongated member with multiple lumens and the proximal region includes multiple elongated member, each defining a lumen. At least one lumen in the distal region is in liquid communication with a lumen from the proximal region. At least two of the elongated members in the proximal region are joined at their proximal ends and form a retraction structure, a structure used for removing the stent from a patient.

25 Claims, 7 Drawing Sheets

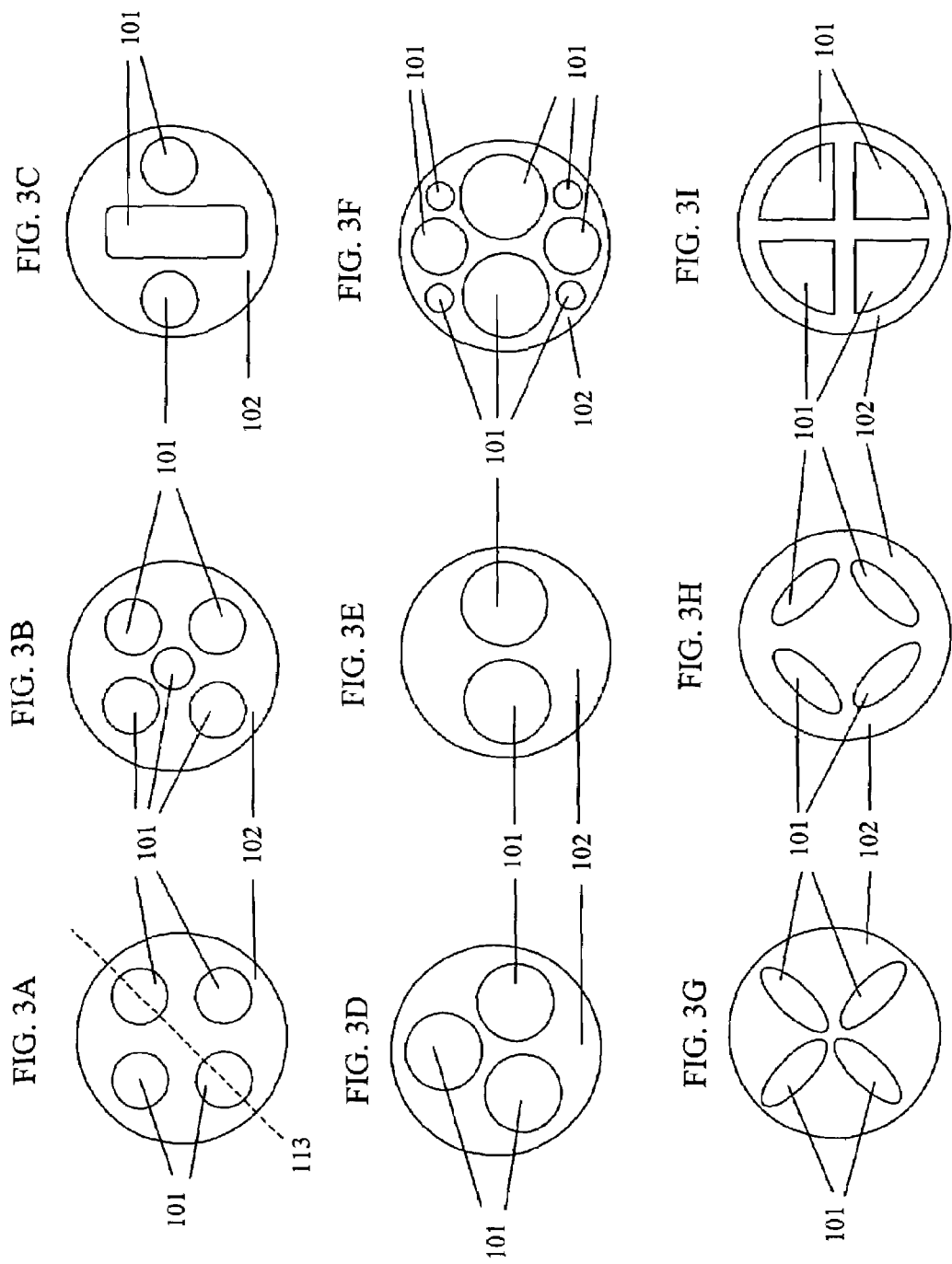

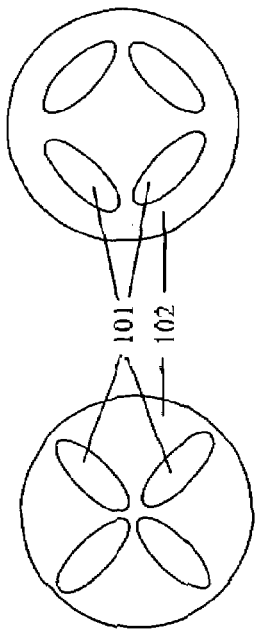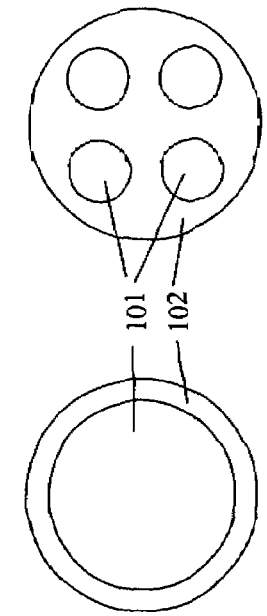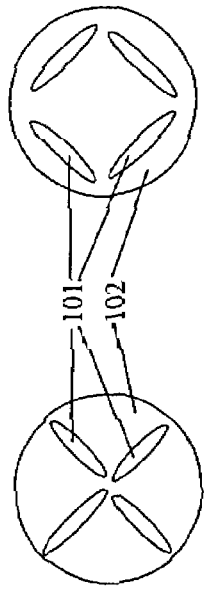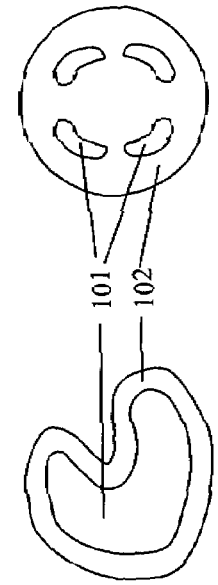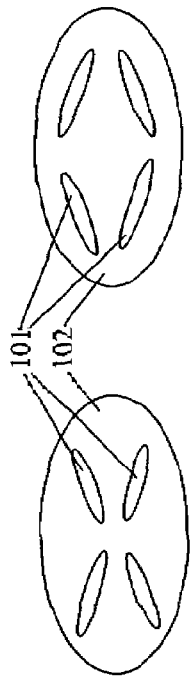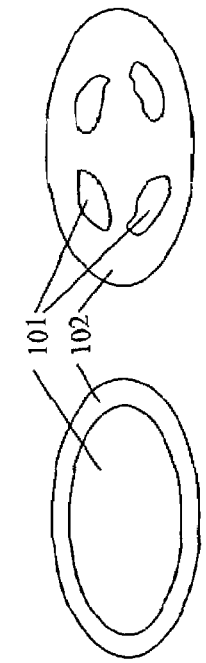

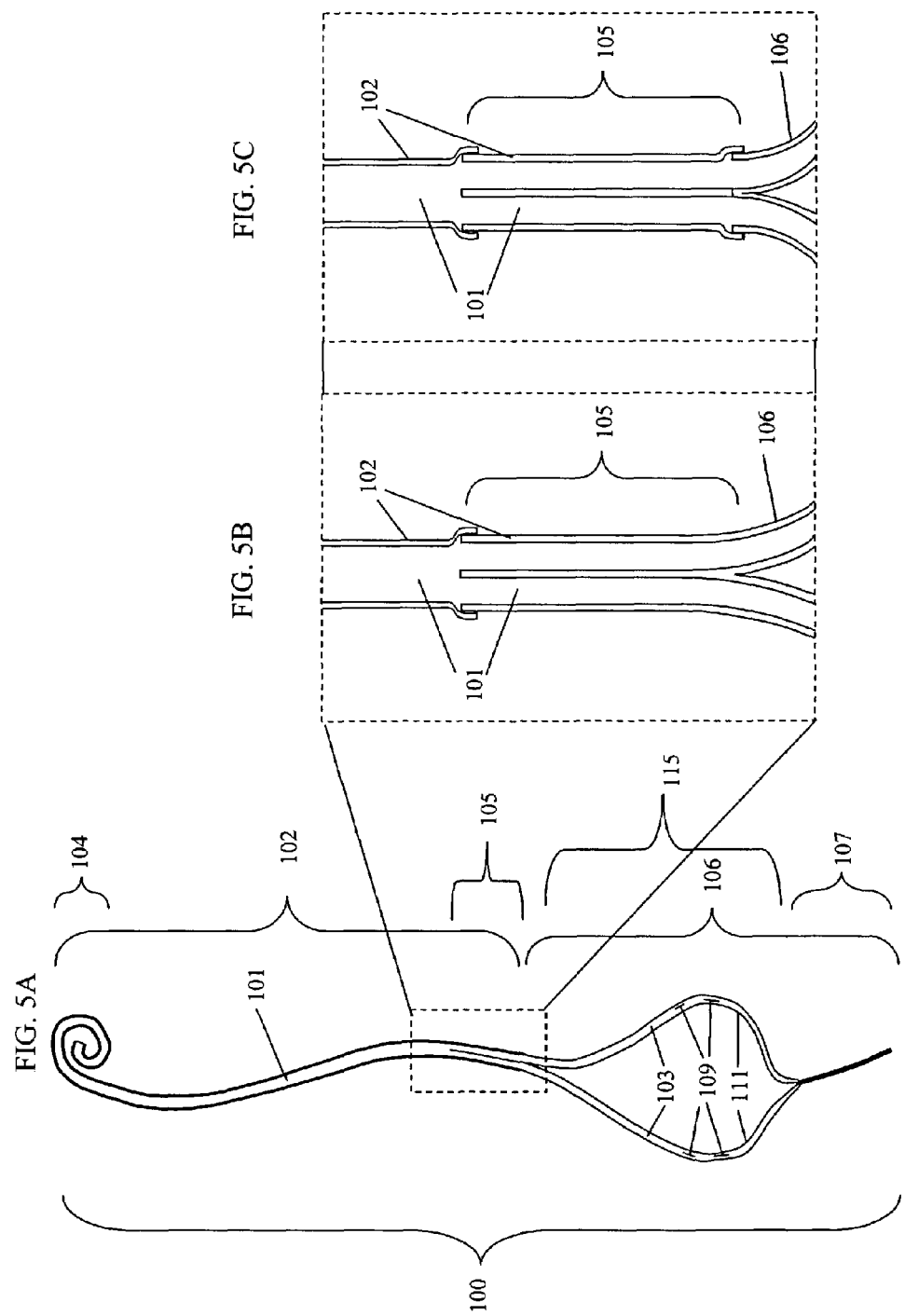

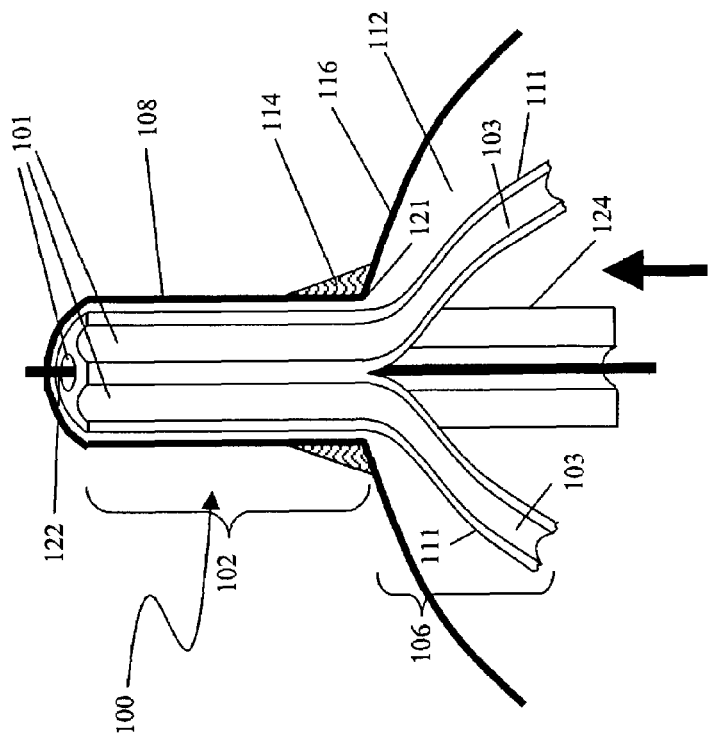
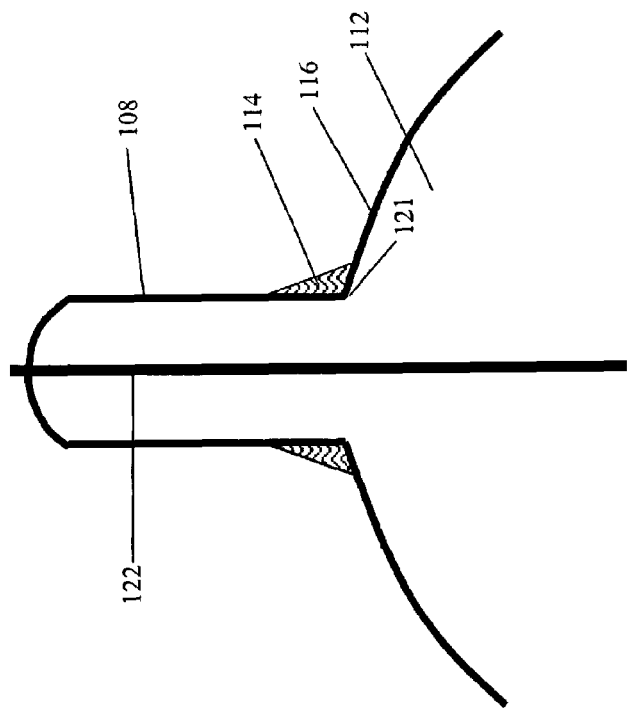

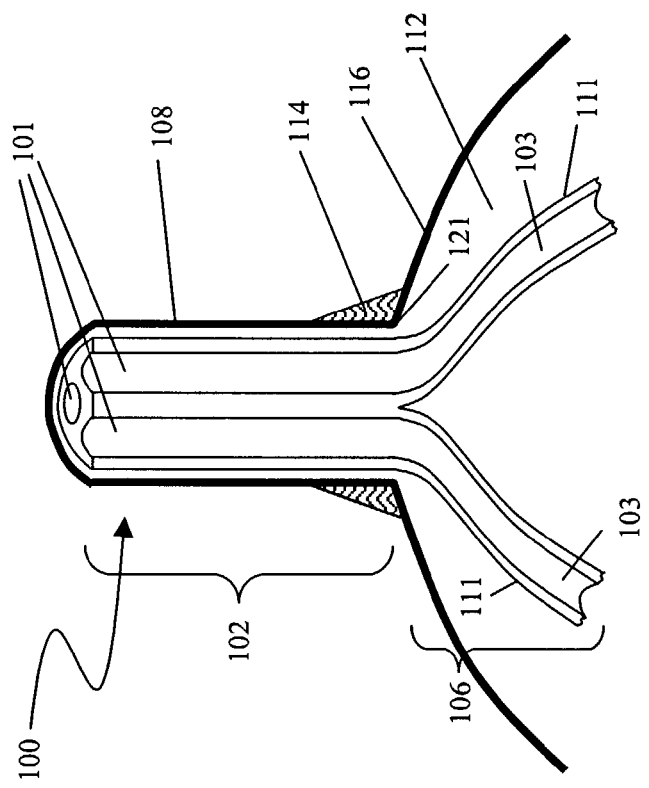
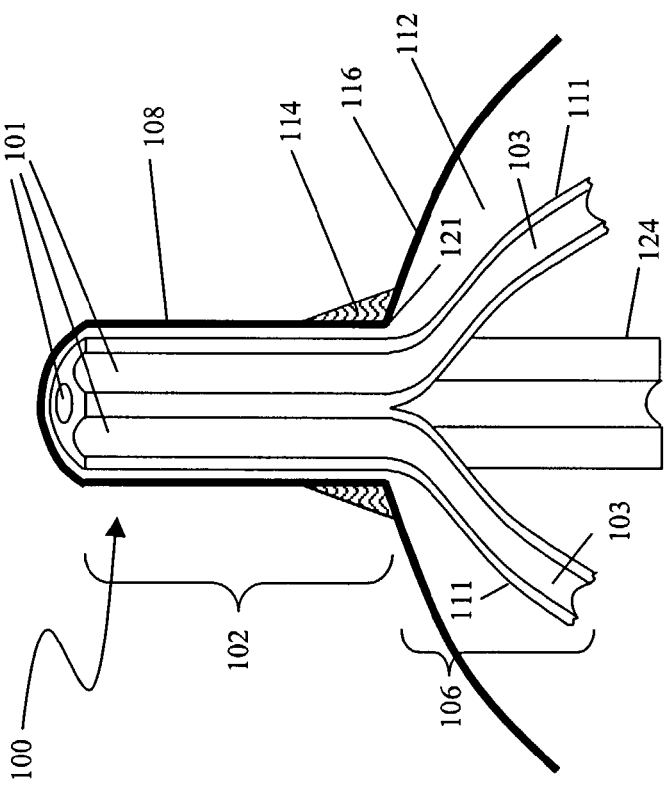
FIG. 6C
FIG. 6D

DRAINAGE DEVICES AND METHODS

TECHNICAL FIELD

This invention generally relates to medical devices for drainage of fluids, and more specifically to ureteral stents.

BACKGROUND INFORMATION

Ureteral stents are used to assist urinary drainage from the kidney to the urinary bladder in patients with a ureteral obstruction or injury, or to protect the integrity of the ureter in a variety of surgical manipulations. Stents may be used to treat or avoid ureteral obstructions (such as ureteral stones or ureteral tumors) which disrupt the flow of urine from the kidneys to the bladder. Serious obstructions may cause urine to back up into the kidneys, threatening renal function. Ureteral stents may also be used after endoscopic inspection of the ureter to prevent obstruction of the ureter by swelling of the ureteral wall caused by the surgical procedure.

Ureteral stents typically are tubular in shape, terminating in two opposing ends: a kidney distal end and a bladder proximal end. One or both of the ends may be coiled in a pigtail or J-shape to prevent the upward and/or downward migration of the stent due, for example, to physiological movements. A kidney end coil resides within the lumen of the kidney, known as the renal pelvis, and is designed to prevent stent migration down the ureter and into the bladder. The bladder-end coil resides in the bladder and is designed to prevent stent migration upward toward the kidney. The bladder coil is also used to aid in retrieval and removal of the stent. Regions such as the trigone region in the bladder and the region of the ureter near the bladder known as the ureteral-vesical junction are particularly innervated and thus sensitive to irritation by foreign objects. Commonly used bladder-end coils contact and irritate the trigone region causing discomfort to the patient. Similarly, the proximal region of the stent contacts the ureteral-vesical junction causing irritation and discomfort to the patient particularly during voiding. Additionally, ureteral stents, particularly the portion positioned within the ureteral-vesical junction and inside the bladder, may produce adverse effects including blood in the urine, a continual urge to urinate, strangury, and flank pain accompanying reflux of urine up the stent (e.g., when voiding). Such effects occur as pressure within the bladder is transmitted to the kidney. In short, while providing drainage from the kidney to the bladder, stents may also cause or contribute to significant patient discomfort and serious medical problems.

SUMMARY OF THE INVENTION

The present invention relates to a ureteral stent that reduces patient discomfort by reducing the flow of urine from the urinary bladder to the kidney (urine reflux) and minimizing contact between the stent and regions of the body of the patient, including the trigone region and ureteral-vesical junction. In particular, the invention relates to a stent with a proximal region that includes a plurality of elongated members, each member defining a lumen, and a distal region that includes an elongated member defining a plurality of lumens. The proximal and distal regions of the stent reduce urine reflux by reducing the rate at which urine may flow through the stent from the urinary bladder to the kidney. Additionally, the proximal and distal regions of the stent minimize the contact and abrasion between these regions of the stent and the trigone region and ureteral-vesical junction of the patient, thus reducing patient discomfort.

The plurality of members in the proximal region are generally located within the urinary bladder when the stent is in place within the urinary tract of a patient. The plurality of elongated members form a proximal retention structure that functions to maintain the proximal region within the bladder and thus restrain the migration of the stent towards the kidney. The shape and composition of the proximal region assist in reducing patient discomfort. The proximal retention structure is formed in a shape that minimizes contact between the elongated members of the proximal retention structure and the trigone region of the bladder, and thus reduces patient discomfort. The elongated members in the proximal region are also sufficiently thin and flexible to minimize the force of contact and abrasion to the sensitive regions of the urinary tract, including the trigone region. However, the plurality of elongated members that form the proximal retention structure are also sufficiently resilient such that the shape of the proximal retention structure is generally maintained while the stent is in the body.

The lumens of the multiple elongated members in the proximal region also reduce patient discomfort caused by urine reflux by minimizing the rate at which urine may flow from the urinary bladder to the kidney. The lumens of the multiple elongated members include sufficiently small inner diameters to prevent the flow of urine from passing through the lumens at a rapid rate typical of urine reflux. However, the size of the lumens are sufficient to allow urine flow to from the kidney to the bladder at the slow rate typical of the naturally occurring drainage from the kidney to the bladder.

The distal region also reduces urine reflux by the multiple lumens in the region preventing the rapid flow of urine, a typical cause of urine reflux. The multiple lumens in the distal region include sufficiently small inner diameters to restrict the rate that urine passes through the distal region. The multiple small lumens in the distal region prevent urine flow at a rate typical of urine reflux. Additionally, the multiple lumens in the distal region assist in preventing urine reflux by becoming occluded as a result of only a moderate degree of compression, by the ureteral orifice, for example. This results from the lumens in the multiple lumen configuration of the distal region collapsing more completely than, for example, a single lumen with a similar lumen capacity under an equivalent amount of compression.

In one aspect, the invention relates to a ureteral stent that includes a proximal region that includes a plurality of elongated members, each of the members defining a lumen extending therethrough, and a distal region disposed relative to the proximal region and that includes an elongated member defining a plurality of lumens extending therethrough. In one embodiment, each lumen in the proximal region is in fluid communication with at least one of the plurality of lumens in the distal region.

In another embodiment, the distal region further comprises a distal retention structure. In one embodiment, the outer dimension of the distal retention structure substantially perpendicular to a longitudinal axis of the elongated member is larger than the diameter of the elongated member. This prevents the entry of the distal retention structure into a ureter. In another embodiment, the distal retention structure includes a coiled shape.

In another embodiment, at least a portion of the distal region includes an elongated member having a single lumen. The single lumen is defined by an inner wall. In a detailed embodiment, the elongated member in the distal region includes an outer diameter ranging from about 6 to about 12 French. This region of the stent may also include a biocompatible plastic. In another embodiment, the elongated members in the proximal region include biocompatible plastic.

In yet another embodiment, the proximal region further includes a proximal retention structure. The proximal retention structure may include, in one embodiment, an outer dimension substantially perpendicular to a longitudinal axis of the elongated member in the distal region that is larger than the diameter of the elongated member in the distal region. Such an outer dimension prevents the entry of the proximal retention structure into a ureter. In one embodiment, the elongated members splay away from a longitudinal axis defined by the elongated member the distal region.

In another embodiment, the proximal region further includes a retraction structure. In one embodiment, the retraction structure includes an elongated member attached to the plurality of elongated members in the proximal region. The retraction structure, in another detailed embodiment, includes an elongated member with an outer diameter less than about 3 French.

In one aspect, the invention relates to a ureteral stent that includes a proximal region that includes a plurality of elongated members, each of the members defining a lumen extending therethrough. The ureteral stent also includes a distal region that includes a first portion, disposed relative to the proximal region, that includes an elongated member defining a plurality of lumens extending therethrough, and a second portion, disposed relative to the first portion, that includes an elongated member defining a lumen extending therethrough. In one embodiment, the proximal region comprises an elongated member in fluid communication with the elongated member of the first portion.

In another embodiment, the second portion of the distal region further includes a distal retention structure. In one embodiment, the outer dimension of the distal retention structure substantially perpendicular to a longitudinal axis of the elongated member in the second portion of the distal region is larger than the diameter of the elongated member in the second portion of the distal region. This prevents the entry of the distal retention structure into a ureter. In yet another embodiment, the distal retention structure includes a coiled shape.

In another embodiment, the proximal region further includes a proximal retention structure. In one embodiment, the outer dimension of the proximal retention structure substantially perpendicular to a longitudinal axis of the elongated member in the distal region is larger than the diameter of the elongated member in the first portion of the distal region. This prevents the entry of the proximal retention structure into a ureter. In yet another embodiment, the proximal region further includes a retraction structure. In one embodiment, the retraction structure includes an elongated member attached to the plurality of elongated members in the proximal region.

In another aspect, the invention relates to a method for draining urine from a kidney. The method requires inserting a ureteral stent into a ureter of a patient wherein the ureteral stent includes a proximal region including a plurality of elongated members, each said member defining a lumen extending therethrough, and a distal region disposed relative to the proximal region and including an elongated member defining a plurality of lumens extending therethrough. The method also requires draining urine via at least one of the plurality of lumens of the distal region. In one embodiment, the stent is positioned such that at least a portion of the distal retention structure resides within a kidney. In another embodiment, the distal region further includes a distal retention structure. The distal retention structure prevents migration of the distal end of the elongated member out of a kidney. In another embodiment, the method further includes positioning at least a portion of the proximal region of the ureteral stent in a urinary bladder. In yet another embodiment, the proximal region further includes a proximal retention structure. The proximal retention structure prevents migration of the proximal end of the ureteral stent out of a urinary bladder.

In another aspect, the invention relates to a method of positioning a ureteral stent within a patient. The method includes providing a ureteral stent as previously described. The method then includes positioning the stent within a patient using a guide wire and a pusher. The stent is mounted over a guide wire already positioned within the body and is pushed along the guide wire utilizing a pusher to locate the stent within the ureter of a patient. The shape of the pusher, particularly the distal end of the pusher, conforms to a shape of a proximal end of the ureteral stent. This allows the pusher to effectively transfer the necessary force to the proximal end of the stent to position the stent within the patient. Once the stent is properly located within patient the guide wire is removed from the patient. The pusher may also be removed from the patient after the procedure.

In one embodiment, the method further includes inserting the guide wire into a urinary tract of the patient. The guide wire may be inserted into the urinary tract prior to inserting the stent into the urinary tract. In yet another embodiment, mounting the stent over a guide wire includes inserting the guide wire within a lumen of the elongated member. In another embodiment, the stent further includes a distal retention structure and the method further includes positioning the distal retention structure within a kidney. The distal retention structure prevents the stent from migrating down the ureter and into the urinary bladder. In yet another embodiment, the stent further includes a proximal retention structure and the method further includes positioning the proximal retention structure in a urinary bladder. The proximal retention structure prevents the stent from migrating out of the bladder and up the ureter.

In another aspect, the invention relates to a method of manufacturing a stent including laminating a plurality of elongated members, each elongated member having a lumen extending therethrough, to form a first elongated member. The method further includes bonding an end of the first elongated member to an end of a second elongated member with a single lumen.

In another aspect, the invention relates to a method of manufacturing a stent including laminating a plurality of elongated members, each elongated member having a lumen extending therethrough, to form a first elongated member. The method also includes bonding a first end of the first elongated member to an end of a second elongated member with a single lumen, and bonding a second end of the first elongated member to an end of a third elongated member with a single lumen.

The foregoing and other aspects, embodiments, features, and advantages of the invention will become apparent from the following description, figures, and claims.

BRIEF DESCRIPTION OF THE DRAWINGS

In the drawings, like reference characters generally refer to the same parts throughout the different views. Also, the drawings are not necessarily to scale, emphasis generally being placed upon illustrating the principles of the invention.

FIGS. 3A-I depict cross-sectional views of various embodiments of a distal region of the ureteral stent of the invention.

FIGS. 4A-L depict cross-sectional views of various embodiments of a distal region of a ureteral stent under different types of compression.

FIGS. 5A-C depict an embodiment of a ureteral stent of the invention, with FIG. 5A showing the device outside of the body, and FIGS. 5B and 5C showing embodiments of a portion of the stent.

FIGS. 6A-D depict various steps involving a guide wire, a pusher and a ureteral stent in longitudinal cross-section positioned in the ureter and urinary bladder, as occurs during installation of the stent.

DESCRIPTION

This invention generally relates to a ureteral stent that minimizes discomfort when positioned within a urinary tract of a patient. The stent of the present invention includes a distal region that includes an elongated member defining multiple lumens. The elongated member of the distal region is connected to a proximal region that includes multiple elongated members, each member defining a lumen. The stent of the invention, due to its dimensions, shape, and rigidity, minimize the force of contact and abrasion to sensitive areas of the urinary tract, including the trigone region of the bladder and ureteral-vesical junction. Additionally, the stent of the invention, due to the multiple lumens in the proximal region and at least a portion of the distal region, reduces urine reflux by reducing the total capacity of the lumens and by facilitating the occlusion of the lumens during compression of the distal region.

Figure 1B:
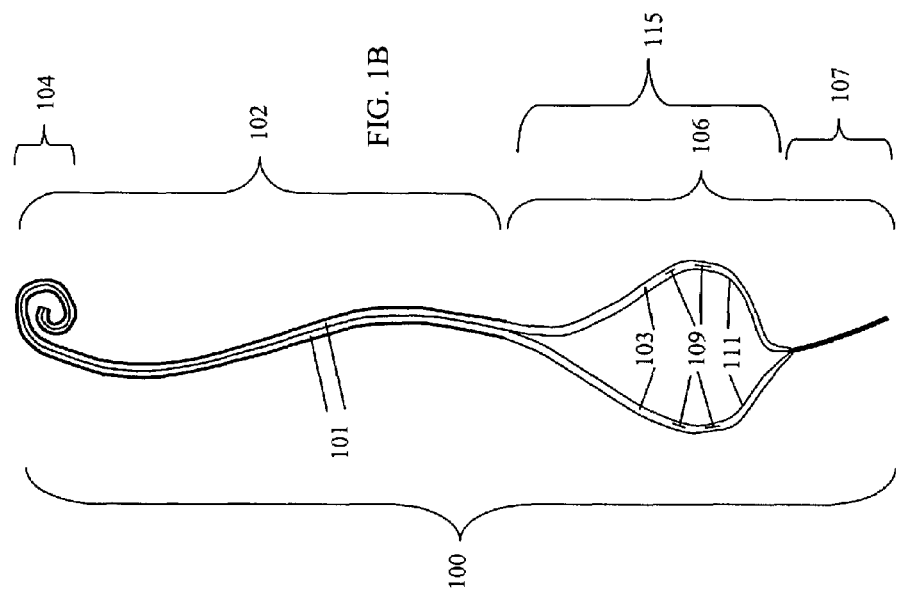
FIGS. 1A and 1B depict an embodiment of a ureteral stent of the invention, with FIG. 1A showing the distal region of the device positioned in a ureter and a kidney and a proximal region of the device in a urethra and bladder, and FIG. 1B showing the device outside of the body.
Figure 1A:
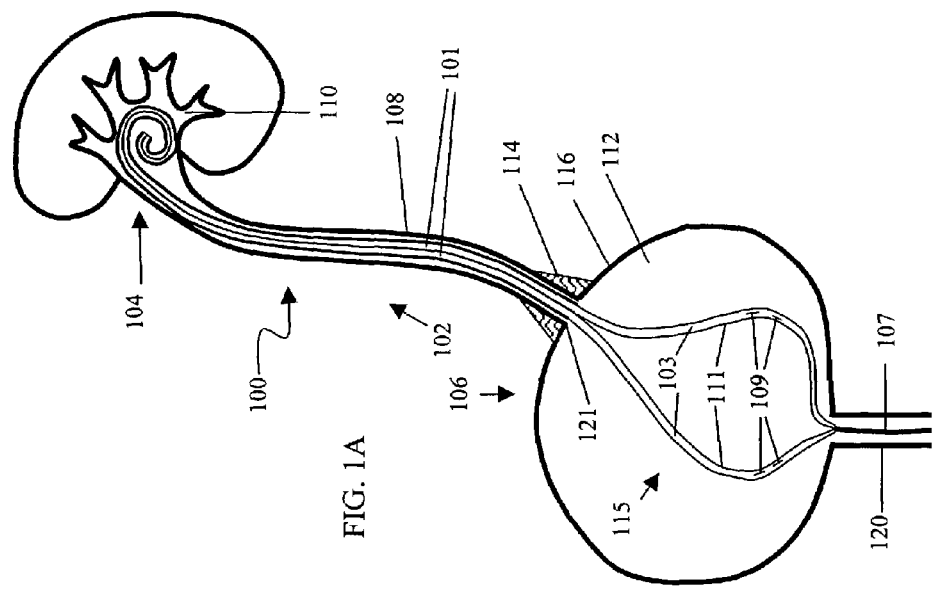

Referring to FIGS. 1A and 1B, a ureteral stent 100 includes a distal region 102 that includes an elongated member defining multiple lumens 101. The stent 100 also includes a proximal region 106 with multiple elongated members 111, (two are depicted) each defining a lumen 103. The lumens 103 of the multiple elongated members 111 are in fluid communication with a lumen 101 of the elongated member of the distal region 102. The elongated members 111 of the proximal region 106 include openings 109, such as slits or holes in the walls of the elongated members 111, for example, to allow urine to drain from the members. Drainage of urine from the renal pelvis 110 to the bladder 112 occurs by the movement of urine into an opening at a distal end of the elongated member of the distal region 102, followed by the urine passing through the distal region 102. The urine then enters and flows through the lumens 103 of the multiple elongated members 111 until reaching the openings 109 in the elongated members 111. Urine may flow out of the openings 109 and into the bladder 112. The urine may then be expelled from the body under the natural control of the patient.

The elongated member of the distal region 102 is located within the ureter 108 and renal pelvis 110 when the stent 100 is positioned in the patient. A portion of the stent 100 at the distal end of the elongated member of the distal region 102 forms a distal retention structure 104. The distal retention structure 104 is located in the renal pelvis 110 and functions as an anchor to prevent the migration of the stent 100 out of the renal pelvis 110 and down the ureter 108. The shape of the distal retention structure 104 may be a coil (shown), a pig-tail coil, J-shaped, or a helical coil, for example.

The elongated members 111 are located within the urinary bladder 112 when the stent 100 is positioned in the patient. The elongated members 111 form a proximal retention structure 115 that functions in retaining the proximal region 106 in the bladder 112 and thus preventing the migration of the stent 100 up the ureter 108. At a proximal end of the proximal region 106 may exist a retraction structure 107. The retraction structure 107 is positioned in the urethra 120 and extends outside of the patient when the stent 100 is positioned in the patient.

The stent 100 of the present invention reduces patient discomfort by minimizing the force of contact and abrasion between the stent 100 and the ureteral-vesical junction 114 and trigone region of the urinary bladder wall 116. The elongated members 111, due to their presence in the bladder 116 when the stent in use, may make contact with the trigone region. The elongated members 111 are generally of minimal diameter, flexible and light in weight thus causing the elongated members 111 to be less irritating or abrasive to the trigone region. The outer diameters of the elongated members 111 and the width of the walls forming the elongated members 111 are sufficiently small to minimize the force of contact and abrasion of the elongated members 111 on the tri gone region of the bladder 112. The elongated members 111 are also sufficiently resilient to maintain a shape suitable to function as a proximal retention structure 115. The elongated members 111 may be formed in various shapes to produce a proximal retention structure 115 that minimizes contact with the trigone region and prevents the movement of the ureteral stent 100 up the ureter 108. The proximal retention structure 115, formed by the elongated members 111, includes an outer dimension greater than the diameter of the ureter 102, thus preventing the proximal retention structure 115 from entering the ureter 102. The elongated members 111 also are joined at the proximal end of the proximal region 106 to form a retraction structure 107. The retraction structure 107, an elongated thread-like member, which need not contain lumens, passes into the urethra 120 from the bladder 112 and extends along the urethra 120 and out of the body of the patient. The retraction structure 107 can be used to withdraw the stent 100 from the patient.

The stent 100 also minimizes patient discomfort associated with urine reflux by assisting in the prevention of urine flow through the stent 100 from the bladder 112 into the renal pelvis 110. During urine reflux through the stent 100, urine must flow into the openings 109 and through the lumens 103 of the elongated members 111 to reach the distal region 102. The elongated members 111 assist in preventing urine reflux by obstructing the rapid passage of urine from the bladder 112 to the distal region 102 of the stent 100. The openings 109 of the elongated members 111, depending on their size, shape and number, may restrict the flow of urine to varying degrees. Reducing the size or number of the openings 109 reduces the rate at which urine may flow into the lumens 103 from the bladder 112. Openings 109 consisting of slits are less open than holes or windows in the elongated members 111 and may restrict urine flow to a greater degree. The diameter of the lumens 103 of the elongated members 111 also affects urine flow. Generally, a reduction in diameter of the lumens 103 reduces the rate of urine flow through the lumens 103. Additionally, the flexibility of the elongated members 111 affects urine flow. Increased flexibility in the elongated members 111 allows the walls of the elongated members 111 to collapse more easily, causing occlusion of the lumens 103 and preventing urine flow. These many characteristics of the elongated members 111 determine the degree to which the route from the bladder 112 to the distal region 102 is restricted or obstructed by the elongated members 111. The characteristics of the elongated members 111 are chosen to provide adequate drainage of urine from the renal pelvis 110 to the bladder 112, to which urine generally flows at a slow rate by wicking or dripping, while acting as a barrier to the rapid flow of urine from the bladder 112 to the renal pelvis 110, as occurs during urine reflux.

The elongated member of the distal region 102 and the proximal region 106 may be constructed of a biocompatible plastic such as but not limited to any of polyester, nylon based biocompatible polymers, polytetrafluoroethylene polymers, silicone polymers, polyurethane polymers, polyethylene polymers, and thermoplastic polymers. The wall of the elongated member of the distal region 102 is of sufficient thickness to resist the pressure from the adjacent tissue caused by a tumor, peristalsis, or swelling, for example, that would collapse the ureter 108 if not for the presence of the stent 100. The renal pelvis 110 and the majority of the ureter 108 are relatively insensitive to irritation by the presence of foreign objects. This allows the elongated member of the distal region 102, which contacts these relatively insensitive regions of the body, to be of relatively large outer diameter and constructed of a relatively stiff material. For example, the outer diameter of the elongated member of the distal region 102 may range from 6-8 French. An acceptable outer diameter of the elongated member of the distal region 102 may also range from 6-12 French, for example. The length of the elongated member of the distal region 102 may vary depending on the size of the patient. An acceptable length of the elongated member in the distal region 102 positions the proximal end of the distal region 102 at a ureteral orifice 121 to the bladder 116. The length of the elongated member of the distal region 102 may range from 20-28 cm, for example. The length of elongated members 111 and the retraction structure 107 in the proximal region 106 may also vary depending on the size of the patient. The elongated members 111 are of sufficient length to form a proximal retention structure 115 that is effective in preventing the upward migration of the stent 100 towards the renal pelvis 110. The length of the elongated members 111 may range from 4-8 cm, for example. The proximal ends of the proximal region 106 may be heat laminated and then stretched to form a retraction structure 107. The stretching process may produce a retraction structure 107 lacking lumens 101 and including an outer diameter smaller than an outer diameter of an elongated member 111. The length of the retraction structure 107 is sufficient to extend along the urethra 120 from the bladder 112 to outside the patient. The outer diameter of the retraction structure 107 is sufficiently small to not prevent a sphincter from constricting the urethra 120 in order to block the flow of urine. The outer diameter of the retraction structure 107 may be less than about 3 French, for example.

Figure 2A:
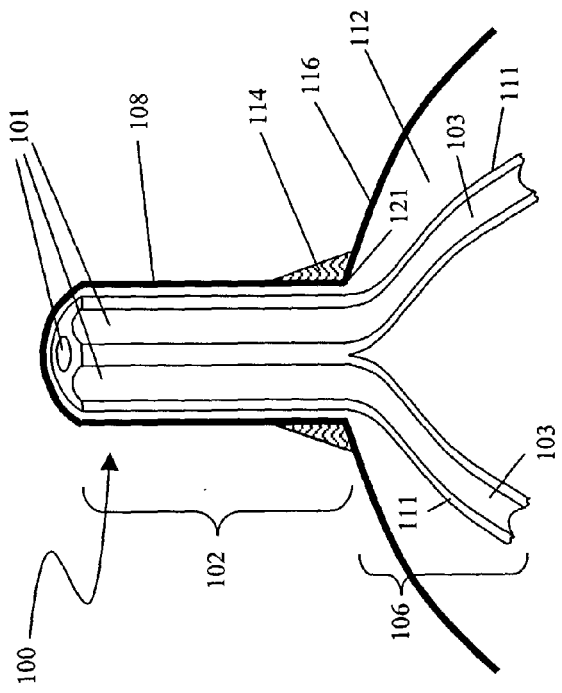
FIGS. 2A and 2B depict an embodiment of proximal and distal regions of a ureteral stent of the invention in longitudinal cross-section within the ureter and urinary bladder.
Figure 2B:
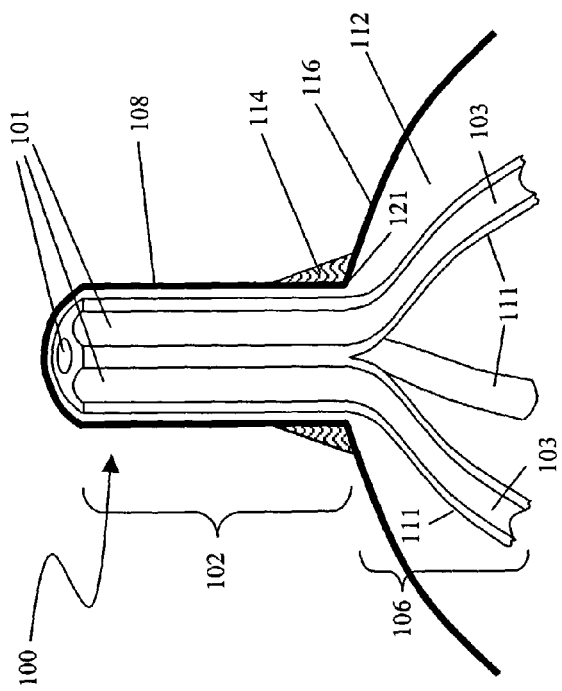

FIGS. 2A and 2B illustrate cross-sectional representations of two embodiments of the stent 100 at the junction of the distal region 102 and proximal region 106, in portions of the ureter 108 and bladder 112. The cross section of the embodiment of the distal region 102 in FIGS. 2A and 2B occurs at the plane 113 (FIG. 3A). In FIG. 2A, all three lumens 101 depicted in the distal region 102 are in fluid communication with the lumens 103 in the elongated members 111. In FIG. 2B, one of the lumens 101 depicted is not connected too or in fluid communication with an elongated member 111. This lumen 101 in the distal region 102 that is not connected to an elongated member 111 may receive a guide wire or other device during the placement of the stent 100 into the body. A lumen 101 not connected to an elongated member 111 also allows for a more unrestricted flow of urine, and thus a potentially increased rate of urine flow through the lumen 101 and stent 100. Additionally, a lumen 101 unattached to an elongated member 111 may allow for easier the passage of stones or calculi through the stent 100.

The elongated member of the distal region 102 minimizes patient discomfort by reducing urine reflux from the bladder 112 to the renal pelvis, particularly during voiding of the bladder. When the stent 100 is in place in the body, a portion of the elongated member of the distal region 102 traverses the ureteral orifice 121 to the bladder 112. The ureteral orifice 121 constricts during voiding of the bladder 112, and thus compresses the portion of the elongated member of the distal region 102 that traverses it. This compression causes the lumens 101 of the elongated member of the distal region 102 to collapse, thus preventing the flow of urine from the bladder 112 to the kidney that causes urine reflux. The multiple lumens 101 of the distal region 102, as compared to a single larger lumen, increase the ability of the stent 100 to seal off urine from entering the kidney during urine reflux.

Referring to FIGS. 3A-I, various configurations of the lumens 101 may exist in the distal region 102. The various configurations may include different numbers of lumens 101 of various sizes in the distal region 102. The lumen capacity of the distal region 102 is herein defined as being proportional to the total lumen area represented in a cross-sectional view of the distal region 102 (FIGS. 3A-3I). The inner diameters or dimensions, the number, and the arrangement of the lumens 101 within the elongated member of the distal region 102 may be varied to alter the rate of urine flow through the stent, the amount that lumen capacity decreases during compression of the distal region 102, and the degree that the distal region 102 irritates the ureteral-vesical junction. The shape of the lumens 101 may be circular, rectangular, and wedge-shaped, for example. Lumens 101 may be shaped specifically to receive or to be compatible with guide wires, cannula, or other devices. The maximum rate of urine flow through the stent is substantially proportional to the lumen capacity. Increasing the number and size of the lumens 101 increases lumen capacity.

Referring to FIGS. 4A-4L, the amount that lumen capacity decreases during compression of the distal region 102 is also affected by the number and size of the lumens 101, as well as by their shape and configuration. An increase in lumen 101 number and a decrease in lumen 101 size generally assist in decreasing lumen capacity during compression of the distal region 102. For example, an elongated member in the distal end 102 with a large single lumen (FIG. 4A) when exposed to a constricting force (FIG. 4E) or a flattening force (FIG. 4I) does not collapse in a manner that substantially occludes the lumen 101. In contrast, examples of elongated members in the distal end 102 with multiple lumens (FIG. 4B-4D) when exposed to a constricting force (FIG. 4F-4H) or a flattening force (FIG. 4J-4L) do collapse in a manner that substantially occludes the lumens 101. The increased ability of the multi-lumen elongated member to collapse and occlude the lumens under intermediate states of compression allows the stent to reduce urine reflux and thus improve patient comfort. Generally, shapes and configurations of the lumens 101 that cause the walls of the lumens 101 to substantially collapse the lumen 101 under a minimal amount of compression of the distal region 102 are the subject of the present invention. FIGS. 3A-F depict various embodiments of shapes and configurations of the lumens 101 that represent a distal region 102, that upon a minimal degree of compression, becomes occluded due to the collapse of the lumens 101. Many variations to the embodiments of the distal region 102 (FIGS. 3A-I) that function similarly are feasible.

The degree that the elongated member of the distal region 102 irritates the ureteral-vesical junction is decreased generally by an increase in the number and size of the lumens 101 in the distal region 102. FIG. 3F depicts an example of such a distal region 102 that includes a relatively large lumen capacity and a correspondingly small amount of structure defining the lumens 101. A distal region 102 with a lesser amount of structure defining the lumens 101 is generally more supple and compressible, and thus less abrasive or irritating to the surrounding tissue of the ureteral-vesical junction. The relative softness of the material comprising the distal region 102 may be chosen in coordination with the configuration of the lumens 101 to achieve the desired physical characteristics in the distal region 102.

A distal region 102 with a relatively larger lumen 101, as depicted in FIGS. 3E and 3F, may allow for the passage of objects such as stones or calculi that would otherwise be caught in a smaller lumen 101. Such a lumen 101 intended for transporting stones may not be connected to an elongated member in the proximal region, thus preventing stones from becoming trapped within an elongated member in the proximal region. Alternatively, a lumen 101 intended for transporting stones may be connected to an elongated member that includes an open proximal end and that is not attached to the retraction structure.

FIGS. 5A and 5B depict a stent 100 that does not include multiple lumens 101 along the entire length of the elongated member of the distal region 102. The enlargement of a portion of the distal region 102 (FIGS. 5B and 5C) depict the junction of a first portion 105 of the distal region 102, that includes multiple lumens 101, with a remaining second portion of the distal region 102, that includes a single lumen 101. The first portion 105 and the second portion of the distal region 102 may be connected as the second portion partially overlaps and is bonded to the first portion 105. The multiple lumens 101 in the first portion 105 assist in the occlusion of the lumen capacity, and thus functions to stem the flow of urine through the stent 100. A single lumen 101 in the second portion of the distal region 102 potentially allows for a larger lumen capacity and thus a greater rate of urine flow through the stent 100 than would be allowed if the second portion of the distal region 102 included multiple lumens 101. A single lumen 101 in the second portion of the distal region 102, which may include the majority of the distal region 102, also makes less likely the occlusion of the lumen 101 by one or more stones or other objects becoming trapped in the lumen 101. Additionally, the single lumen 101 in the second portion of the distal region 102 is less likely to be collapsed and occluded by a compression, caused by the surrounding tissue of the ureter, for example. Thus, a single lumen 101 extending along the second portion of the distal region 102 increases the ability of the stent 100 to drain urine and stones from the renal pelvis to at least the ureteral orifice.

The manufacture of a stent 100, which includes a different wall thickness and/or composition in the second portion of the distal region 102 than in the proximal region 106, is simplified when the stent 100 is constructed from two or more segments as depicted in FIGS. 5A-C. In constructing the stent 100, the number of elongated members 111, their wall thickness, and their composition is selected to maximize the functions of the proximal region 106. A plurality of elongated members 111 are laminated, by heating, for example, along their distal end to form a relatively short elongated member with multiple lumens 101 connected to the elongated members 111 of the proximal region 106. The relatively short elongated member with multiple lumens 101 forms the first portion 105 of the distal region 102. The first portion 105 is bonded to the second portion of the distal region 102 to form the stent 100 (FIGS. 5A and 5B). In another embodiment, the first portion 105 is constructed by the lamination of a plurality of relatively short elongated members resulting in a relatively short elongated member with multiple lumens 101. The relatively short elongated member with multiple lumens 101 forms the first portion 105 and is bonded to the proximal region 106 and to the second portion of the distal region 102 (FIG. 5C). This allows the three segments (second portion of the distal region 102, first portion 105, and proximal region 106) to be individually constructed to different specifications and with different materials and subsequently assembled into a single stent 100. Additionally, heating and extruding a proximally located portion of the proximal region 106 may form a retraction structure 107.

Referring to FIGS. 6A-D, the method of positioning a ureteral stent 100 within a patient is illustrated in a schematic with cross-sectional views of portions of the ureter 108 and urinary bladder 112. Draining urine from the kidney or ureter 108 may be accomplished by inserting a ureteral stent 100 according to the invention over a guide wire 122 with a pusher 124, through the urethra and urinary bladder 112 to the final position in the ureter 108. A guide wire 122 (FIGS. 6A and 6B) assists in the installation of the stent 100 by providing a mechanical means of directing the stent 100 into the patient. The guide wire 122 is inserted into the body, through the urinary bladder 112 and ureter 108 until reaching the renal pelvis (FIG. 6A). Once the guide wire 122 is positioned in the patient, the stent 100 is inserted into the patient over the guide wire 122, which remains outside the body (FIG. 6B). The distal retention structure 104 is straightened as the guide wire 122 is inserted through a lumen 101 without an attached elongated member 111, and the stent 100 is moved along the length of the guide wire 122 and into the body with a pusher 124. The guide wire 122 may not enter the proximal region 106 at any time. Rather, the proximal region 106, including the elongated members 111 and the retraction structure, is positioned in the body as a result of being attached to the elongated member of the distal region 102.

Once the ureteral stent 100 is properly positioned, the guide wire 122 may be removed (FIG. 6C). The ureteral stent 100 may also be inserted into the patient by use of an endoscope, ureteroscope, or a cytoscope, for example. Once the guide wire 122 is removed, the pusher 124 may be withdrawn from the body of the patient (FIG. 6D).

Referring to FIG. 1A, the distal retention structure 104 is constructed from resilient material that regains its initial shape after distortion. The distal retention structure 104 assumes its predetermined shape within the renal pelvis and thus prevents the stent 100 from migrating down the ureter 108. The outer dimension of the distal retention structure 104 is larger than the outer diameter of the elongated member of the distal region 102. The proximal retention structure 115 formed by the elongated members 111 is located in the bladder 112.

Referring again to FIGS. 2A, 2B, and 3A-I, the proximal region 106 may adopt a variety of shapes and configurations. Referring to FIGS. 6B and 5C, the pusher 124 abuts and applies a force against the proximal end of the elongated member of the distal region 102 to push the stent 100 into the body of the patient. To facilitate positioning of the stent 100 in the patient's body, the distal end of a pusher 124 conforms to the proximal end of the elongated member of the distal region 102. In particular, the distal end of a pusher 124 accommodates the multiple elongated members 111 that attach to the proximal end of the elongated member of the distal region 102. This allows for the force applied to the pusher 124 to be effectively transferred to the ureteral stent 100 during installation of the stent 100. Additionally, the lumen of the pusher 124 is large enough to house the guide wire 122 (FIG. 6B).

Referring again to FIGS. 1A and 1B, the distal region 102 and proximal region 106 are constructed of a biocompatible plastic such as but not limited to any of polyester, nylon based biocompatible polymers, polytetrafluoroethylene polymers, silicone polymers, polyurethane polymers, polyethylene polymers, and thermoplastic polymers.

Referring to FIGS. 5A and 5B, the construction of the stent 100 includes bonding a component that includes the proximal region 106 and the portion 105 of the distal region 102 comprising multiple lumens 101, to the single lumen 101 portion of the distal region 102. Additionally, portion 105 may also be bonded to the proximal region 106 (FIG. 5C). The bonding of these components may be performed by heat bonding. Heat bonding functions by partially melting the plastic of a structure, allowing the melted plastic to adhere to a contacting surface or component, and allowing the plastic to cool and harden and thus form a bond. Heat bonding methods that include radio frequency bonding, induction heating and conduction heating may be used. The plastic of a first component may be selected to melt at a similar temperature as a second component so that both components are melted during the heat bonding process. Alternatively, either the first or second component may be constructed from plastic with a lower melting temperature than the other component in order that only the component with the lower melting temperature may melt during the bonding process.

Alternatively, the components may be bonded by the use of a bonding solvent, such as cyclohexanone and methylethylketone, for example. The bonding solvent acts by dissolving and swelling the plastic of the components. As the plastic of the components dissolve and swell, the components adhere to each other. The solvent is then removed allowing for the dissolved and swollen plastic to harden and thus complete the bonding process.

Having thus described certain embodiments of the present invention, various alterations, modifications, and improvements will be apparent to those of ordinary skill. Such alterations, modifications, and improvements are intended to be within the spirit and scope of the invention. Accordingly, the foregoing description of embodiments of the invention is not intended to be limiting.

What is claimed is:

1. A ureteral stent comprising:
   a distal region including an elongated member defining a longitudinal axis and at least one lumen that is configured to convey liquid; and
   a proximal region in fluid communication with the distal region and comprising a proximal retention structure that includes a plurality of elongated members that splay away from the longitudinal axis of the elongated member of the distal region to help prevent entry of the proximal retention structure into a ureter, at least two of the elongated members of the proximal region having a lumen extending therethrough each of which is configured to convey liquid and is in fluid communication with the at least one lumen of the elongated member of the distal region,
   a distal end of a first elongated member from the plurality of elongated members of the proximal retention structure being coupled to a distal end of a second elongated member from the plurality of elongated members of the proximal retention structure,
   a proximal end of the first elongated member from the plurality of elongated members of the proximal retention structure being coupled to a proximal end of the second elongated member from the plurality of elongated members of the proximal retention structure,
   a central portion of the first elongated member from the plurality of elongated members of the proximal retention structure being unattached from a central portion of the second elongated member from the plurality of elongated members of the proximal retention structure,
   a portion of the first elongated member of the plurality of elongated members of the proximal retention structure being configured to be disposed in a bladder, the portion of the first elongated member of the plurality of elongated members of the proximal retention structure defining an opening such that the lumen of the first elongated member is in fluid communication with the bladder.

2. The ureteral stent of claim 1, wherein an outer dimension of the plurality of elongated members is greater than a diameter of the ureter.

3. The ureteral stent of claim 1, wherein the plurality of elongated members includes an outer dimension substantially perpendicular to the longitudinal axis of the elongated member of the distal region.

4. The ureteral stent of claim 1, wherein the plurality of elongated members of the proximal region are sufficiently resilient to generally maintain a shape of the proximal retention structure.

5. The ureteral stent of claim 1, wherein the proximal region includes a retraction structure coupled to at least one of the elongated members from the plurality of elongated members of the proximal retention structure.

6. The ureteral stent of claim 1, wherein the proximal region includes a retraction structure, a distal end of the retraction structure coupled to at least one of the elongated members from the plurality of elongated members of the proximal retention structure, a proximal end of the retraction structure configured to be disposed outside of a body.

7. The ureteral stent of claim 1, wherein the opening is defined by a side wall of the portion of the first elongated member, the opening having a length that is substantially greater than a width of the opening.

8. The ureteral stent of claim 1, wherein the central portion of the first elongated member from the plurality of elongated members of the proximal retention structure is biased away from the central portion of the second elongated member from the plurality of elongated members of the proximal retention structure.

9. The ureteral stent of claim 1, wherein the central portion of the first elongated member from the plurality of elongated members of the proximal retention structure is movable with respect to the central portion of the second elongated member from the plurality of elongated members of the proximal retention structure.

10. A ureteral stent, comprising:
    a distal region including an elongated member defining a longitudinal axis and at least one lumen that is configured to convey liquid; and
    a proximal region in fluid communication with the distal region and comprising a proximal retention structure that includes a plurality of elongated members, a central portion of a first elongated member from the plurality of elongated members being unattached and biased away from a central portion of a second elongated member from the plurality of elongate members, the plurality of elongated members being sufficiently resilient to generally maintain a shape of the proximal retention structure while the stent is in a patient's body, at least two of the elongated members of the proximal region including a side wall that defines a lumen configured to convey liquid and an opening having a length that is substantially greater than a width of the opening.

11. The ureteral stent of claim 10, wherein an outer dimension of the proximal retention structure is greater than a diameter of a ureter.

12. The ureteral stent of claim 10, wherein at least two of the lumens of the elongated members of the proximal region are in fluid communication with the at least one lumen of the elongated member of the distal region.

13. The ureteral stent of claim 10, wherein:
the at least one lumen is a first lumen; and
the elongated member of the distal region defines a second lumen, the first lumen in fluid communication with the lumens of the at least two elongated members of the proximal region, the second lumen in fluid communication with a bladder.

14. The ureteral stent of claim 1, wherein the central portion of the first elongated member is separated from the central portion of the second elongated member.

15. The ureteral stent of claim 1, wherein the central portion of the first elongated member is movable with respect to the central portion of the second elongated member.

16. The ureteral stent of claim 10, wherein a distal end of the first elongated member is coupled to a distal end of the second elongated member, a proximal end of the first elongated member is coupled to a proximal end of the second elongated member, and the central portion of the first elongated member is separated from the central portion of the second elongated member of the proximal region.

17. A ureteral stent comprising:
a distal region having an elongated member, the elongated member having at least a first lumen, a second lumen and a third lumen configured to convey liquid, the distal region defining an opening to provide fluid communication between the third lumen and a bladder, the distal region including a coil shaped retention structure; and
a proximal region having a first elongated member and a second elongated member, the first elongated member and the second elongated member each having a lumen configured to convey liquid, the first lumen of the elongated member of the distal region being in fluid communication with the lumen of the first elongated member of the proximal region, the second lumen of the elongated member of the distal region being in fluid communication with the lumen of the second elongated member of the proximal region,
the first elongated member and the second elongated member of the proximal region each including a side wall defining an opening having a length that is substantially greater than a width of the opening.

18. The ureteral stent of claim 17, wherein a portion of the first elongated member of the proximal region is disposed apart from a portion of the second elongated member of the proximal region.

19. The ureteral stent of claim 17, wherein the first elongated member of the proximal region and the second elongated member of the proximal region are configured to help retain the proximal region within the bladder.

20. The ureteral stent of claim 17, wherein the first elongated member of the proximal region and the second elongated member of the proximal region are configured to splay away from a longitudinal axis of the distal region to help prevent entry of the proximal region into a ureter.

21. The ureteral stent of claim 17, wherein a diameter of the third lumen of the elongated member of the distal region is larger than a diameter of the first lumen of the elongated member of the distal region and a diameter of the second lumen of the elongated member of the distal region.

22. The ureteral stent of claim 17, wherein a diameter of the third lumen of the elongated member of the distal region is configured to convey a kidney stone.

23. The ureteral stent of claim 17, wherein a distal end of the first elongated member of the proximal region is coupled to a distal end of the second elongated member of the proximal region, a proximal end of the first elongated member of the proximal region is coupled to a proximal end of the second elongated member of the proximal region, and a central portion of the first elongated member of the proximal region is biased away from a central portion of the second elongated member of the proximal region to help prevent entry of the proximal region into a ureter.

24. The ureteral stent of claim 17, wherein a distal end of the first elongated member of the proximal region is coupled to a distal end of the second elongated member of the proximal region, a proximal end of the first elongated member of the proximal region is coupled to a proximal end of the second elongated member of the proximal region, and a central portion of the first elongated member of the proximal region is separated from a central portion of the second elongated member of the proximal region to help prevent entry of the proximal region into a ureter.

25. The ureteral stent of claim 17, wherein a distal end of the first elongated member of the proximal region is coupled to a distal end of the second elongated member of the proximal region, a proximal end of the first elongated member of the proximal region is coupled to a proximal end of the second elongated member of the proximal region, and a central portion of the first elongated member of the proximal region is movable with respect to a central portion of the second elongated member of the proximal region to help prevent entry of the proximal region into a ureter.

* * * * *